(12) United States Patent
Ashkenasi et al.

(10) Patent No.: US 7,751,668 B2
(45) Date of Patent: Jul. 6, 2010

(54) MICROSTRUCTURING OF AN OPTICAL WAVEGUIDE FOR PRODUCING FUNCTIONAL OPTICAL ELEMENTS

(75) Inventors: David Ashkenasi, Berlin (DE); Arkadi Rosenfeld, Berlin (DE); Verena Knappe, Berlin (DE); Gerhard Müller, Berlin (DE)

(73) Assignee: CeramOptec Industries, Inc., East Longmeadow, MA (US)

( * ) Notice: Subject to any disclaimer, the term of this patent is extended or adjusted under 35 U.S.C. 154(b) by 551 days.

(21) Appl. No.: 10/520,336

(22) PCT Filed: Jul. 4, 2003

(86) PCT No.: PCT/EP03/07183

§ 371 (c)(1),
(2), (4) Date: Aug. 22, 2005

(87) PCT Pub. No.: WO2004/005982

PCT Pub. Date: Jan. 15, 2004

(65) Prior Publication Data

US 2006/0147170 A1 Jul. 6, 2006

(30) Foreign Application Priority Data

Jul. 5, 2002 (DE) ................. 102 31 463

(51) Int. Cl.
*G02B 6/10* (2006.01)
(52) U.S. Cl. .................... 385/129
(58) Field of Classification Search ........... 385/129
See application file for complete search history.

(56) References Cited

U.S. PATENT DOCUMENTS 4,466,697 A 8/1984 Daniel (Continued)

FOREIGN PATENT DOCUMENTS

DE 197 39 456 A1 3/1999

(Continued)

OTHER PUBLICATIONS

Stuart, et al., "Laser-Induced Damage in Dielectrics with Nanosecond to Subpicosecond Pulses," The American Physical Society, Physical Review Letters, vol. 74, No. 12, p. 2248-2251, (Mar. 20, 1995).

(Continued)

*Primary Examiner*—Mark A Robinson
*Assistant Examiner*—Erin D Chiem
(74) *Attorney, Agent, or Firm*—Bolesh J. Skutnik; B J Associates

(57) ABSTRACT

The invention relates to a method for microstructuring an optical waveguide having a first cross-sectional region with a first refractive index, a second cross-sectional region with a second refractive index, and a boundary region in the transition from the first to the second cross-sectional region, in which the optical waveguide is exposed to laser radiation in the form of at least one ultra-short single pulse or a sequence of pulses with a defined energy input, whereby the radiant exposure takes place in such a manner that a modification of at least one optical property of the optical waveguide takes place at at least one defined portion of the boundary region.

19 Claims, 2 Drawing Sheets

U.S. PATENT DOCUMENTS

| | | |
|---|---|---|
| 6,384,977 B1 | 5/2002 | Laming et al. |
| 6,573,026 B1 * | 6/2003 | Aitken et al. ................ 430/290 |
| 2001/0021293 A1 | 9/2001 | Kouta et al. |
| 2002/0085824 A1 | 7/2002 | Dugan et al. |

FOREIGN PATENT DOCUMENTS

| | | |
|---|---|---|
| EP | 1 116 965 A1 | 7/2001 |
| WO | WO 99/23041 | 5/1999 |
| WO | WO 00/79319 A1 | 12/2000 |
| WO | WO-0079319 A1 * | 12/2000 |
| WO | WO 01/09899 A1 | 2/2001 |

OTHER PUBLICATIONS

International Search Report for International Application No. PCT/EP03/07183 (Jan. 14, 2004).

* cited by examiner

MICROSTRUCTURING OF AN OPTICAL WAVEGUIDE FOR PRODUCING FUNCTIONAL OPTICAL ELEMENTS

The invention relates to a method for microstructuring an optical waveguide with a first cross-sectional region having a first refractive index, a second cross-sectional region having a second refractive index and a boundary region in the transition from the first to the second cross-sectional region, in which the optical waveguide is exposed to laser radiation in the form of at least one ultra-short single pulse or a sequence of pulses with defined energy input. The invention also relates to an optical functional element having an optical waveguide. The invention also relates to a device for microstructuring an optical waveguide with laser radiation.

BACKGROUND OF THE ART

A method of the type mentioned at the beginning is known from DE 197 39 456. In accordance with it, a modification is produced in a core of an optical waveguide with a single pulse or a sequence of pulses having a defined number of pulses. The optical waveguide core is surrounded by an optical waveguide cladding, the material of which has a lower refractive index than that of the optical waveguide core. The pulse intensity is chosen so that the destruction threshold is exceeded with each single pulse. By a micro-explosion in the material, scattering centres are produced, which effect a scattering of a part of the radiation guided in the optical waveguide core in all directions. From the article Physical Review Letters, Vol. 74 (1995), pages 2248 to 2251 is known the use of laser pulses having a duration of a few 10 ns down into the sub-picosecond range for material changes in the micrometer range by virtue of the low energy.

The production of grating structures in an optical waveguide is known from U.S. Pat. No. 6,384,988. The optical waveguide consists of a photosensitive material, which is illuminated according to the grating structure.

The last-named method has the disadvantage that it can only be used with photosensitive optical waveguide materials. The other mentioned methods from the prior art do not enable any controlled coupling of light out of the optical waveguide or coupling of light into the optical waveguide. The method of DE 107 39 456 only allows the scattering of light from the optical waveguide in all directions.

SUMMARY OF THE INVENTION

The object of the invention is to provide a method for the microstructuring of an optical waveguide of the type mentioned at the beginning which does not have the mentioned disadvantages. Another object of the invention is to provide an optical functional element with an optical waveguide, which enables a (particularly directional-selective) coupling of light out of an optical waveguide or coupling of light into an optical waveguide. Another object of the invention is to provide a device for the microstructuring of an optical waveguide with laser radiation, which enables the manufacture of optical functional elements with the mentioned properties.

In accordance with a first aspect of the invention, the object is achieved by a method for the microstructuring of an optical waveguide with a first cross-sectional region having a first refractive index, a second cross-sectional region having a second refractive index, and a boundary region in the transition from the first to the second cross-sectional region, in which the optical waveguide is exposed to laser radiation in the form of at least one ultra-short single pulse or a single pulse with a defined energy input, whereby the radiation takes place in such a manner that a modification of at least one optical property of the optical waveguide occurs at one defined portion at least of the boundary region.

The method according to the invention is distinguished by the fact that the optical waveguide is modified not in the interior of a cross-sectional region, such as, for example, the core of the optical waveguide, but in defined manner in the boundary region between the first and the second cross-sectional region, i.e. for example at the boundary surface between the optical waveguide core and the optical waveguide cladding. The first cross-sectional region may thus be, for example, an optical waveguide core with a refractive index $n_1$ and the second cross-sectional region may be an optical waveguide cladding with a refractive index $n_2 < n_1$. In this case radiation takes place in such a manner that a modification of at least one optical property of the optical waveguide occurs at one defined portion at least of the boundary region.

A permanent change in a value of an optical parameter of the optical waveguide is understood as a change in an optical property of the optical waveguide. Such an optical parameter is, for example, the refractive index of the material of the first or second cross-sectional region. With a change in the refractive index in the boundary region between the first and the second cross-sectional region, the reflection of a light beam guided in the first cross-sectional region can be influenced in a purposeful manner at the boundary surface to the second cross-sectional region. This may occur, for example, in such a manner that instead of total reflection of the light conveyed in the first cross-sectional region, only a reflection of a part of the light intensity striking the boundary region occurs. This results in that a part of the light conveyed in the first cross-sectional region is coupled out of said region. Depending on the arrangement and construction of the modified portion of the boundary region, irradiation in a specific direction and in a determined intensity ratio to the light intensity conveyed in the optical waveguide can be achieved thereby.

With the method according to the invention, an optical waveguide is structured on a micro-optical scale, which has a first cross-sectional region with a first refractive index, a second cross-sectional region with a second refractive index and a boundary region in the transition from the first to the second cross-sectional region. The boundary region in the transition from the first to the second cross-sectional region forms a boundary surface in the ideal case. However, it is obvious that a boundary surface can only be modified by the boundary region around the boundary surface being modified. This means that a portion of the first cross-sectional region close to the boundary surface or a portion of the second cross-sectional region close to the boundary surface or respectively a portion in both cross-sectional regions close to the boundary surface is modified.

However, the method according to the invention is not suitable just for use in the microstructuring of an optical waveguide with a step-shaped refractive index profile. It may also be used with an optical waveguide having a continuous cross-sectional profile of the refractive index. The boundary region in which a modification of at least one optical property of the optical waveguide is produced is in this case a preselectable region in a depth portion of the optical waveguide. In this case the modifications thus lie beneath the surface in the optical waveguide with a gradient index profile.

In a preferred embodiment of the invention, the modification of at least one optical property of the optical waveguide lies in the creation of a scattering centre by micro-damage or by removal of material in the boundary region. Removal of material may take place by a micro-explosion, for example.

In another preferred embodiment of the method according to the invention, the modification is a transformation of the phase of the material of the first cross-sectional region or of the material of the second cross-sectional region or of the phase of both cross-sectional regions.

The controlled production of a modification in accordance with the above-mentioned embodiments, i.e. change in refractive index, production of a scattering centre by micro-damage or phase transformation, takes place in a preferred exemplified embodiment of the method in which the laser radiation is chosen in such a manner that, at the defined portion of the boundary region provided for the modification, a charge carrier plasma is produced, for example an electron plasma, with a charge carrier density depending on the desired modification is produced.

Since the energy transfer out of the laser beam into the material and thus the material reaction or material modification is dependent on the induced plasma, the use of suitable laser pulses is necessary to control the plasma density. The interaction between the laser radiation and the material for the manufacture of optical waveguides greatly depends on the ratio of the energy density to the selected power density of the respective laser radiation. Only the use of time-modulated laser radiation increases the ratio between the power density and the energy density of a laser pulse (also called "single pulse". To achieve the modifications provided in accordance with the invention in the boundary region, it is necessary to work with high power density with a low energy density and thus to create the condition for controlling the plasma density.

The high power density of the laser beam that can be achieved with ultra-short laser pulses induces non-linear optical effects of the excitation at the defined site in the boundary region or in the interior of the material, so that a very local energy effect takes place in the otherwise transparent material. Changes in the optical properties, which are also known as modifications, may thus be achieved at the defined site depending on the material combination and the power density.

The laser radiation therefore preferably has a power density of roughly $10^{10}$ W/cm$^2$ or of more than $10^{10}$ W/cm$^2$. In this power density range an efficient coupling-in of the laser energy is predominantly produced via non-linear optical effects, such as multiphoton absorption, tunnel and cascade ionisation.

The mentioned power density may be achieved with appropriate focusing of the laser radiation with laser pulses having a duration of $10^{-10}$ seconds and an energy of roughly 10 nanojoules (nj) or less than 10 nj. The pulse length is chosen according to the desired plasma density. The laser pulse durations used are preferably between 0.1 and 50 picoseconds.

In this case the wavelength of the laser radiation is preferably chosen so that the optical waveguide in the light path to the defined portion of the boundary region is transparent or partially transparent for light of the chosen wavelength up to a power density critical for the control of the plasma density, thus for example the mentioned power density of roughly $10^{10}$ W/cm$^2$. The component consequently remains transparent on the light path until the laser radiation reaches a power density in the mentioned range by virtue of the increasing focusing.

The choice of the light wavelength is consequently also dependent on the respective material of the cross-sectional regions penetrated by radiation.

The focusing of the laser beam onto the defined portion of the boundary region preferably takes place by using a microscope lens.

In a preferred refinement of the method, a laser beam is directed so that it enters the optical waveguide at an angle of 90° to an outer face of the optical waveguide at the point of impact. However, other embodiments of the laser beam guidance are also possible. The laser beam can also enter the optical waveguide at another angle. Instead of a microscope lens or in addition thereto, focusing of the laser beam may also be achieved with a mirror lens system in the defined portion of the boundary region. It just depends on power density which is sufficient to control the plasma density at the defined portion of the boundary region.

In another preferred embodiment of the invention, a laser beam is conveyed through an immersion fluid before it enters the optical waveguide.

In another preferred embodiment of the invention, the laser beam is moved relative to the optical waveguide or the optical waveguide is moved relative to the laser beam. Thus more complicated modification structures can also be achieved by machine production. The optical waveguide may, for example, be rotated relative to the laser beam and/or displaced in its longitudinal direction. In this manner modifications can be performed at any point of the boundary region in any form both only as a change in the refractive index and also in the form of solid scattering centres and also in the form of phase transformations or as a combination of two or all three mentioned modifications.

In an optical waveguide which has, seen in cross section from the interior outwards, more than two cross-sectional portions with different refractive indices and accordingly also several boundary regions of adjacent cross-sectional portions, modifications at more than one boundary region may be provided by corresponding variations in the focusing.

The same applies for an optical waveguide having a continuous cross-sectional profile of the refractive index. Here too, modifications in several previously selected cross-sectional portions may take place by different focusing. It is obvious that, with such a gradient index fibre, these cross-sectional regions correspond to the boundary region of the embodiments of the invention which produce modifications in an optical waveguide having a step-shaped refractive index profile.

Optical functional elements can be manufactured with the microstructuring method according to the invention. The arrangement and structure of the modifications depends on the desired functional element.

Thus in one embodiment of the invention it is provided that the modifications be circumferentially disposed, so that with a coupling-out element a defined irradiation takes place in the radial direction in a defined lengthwise portion of the optical waveguide. This may be provided, for example, in a scattered light applicator, as is used in medical engineering for the introduction of laser light into tissue.

Another embodiment provides introducing the modifications in the optical waveguide in a defined selected manner at an extremely limited position, so that irradiation only takes place in one direction, or so that this site may serve as an inward coupling element. Other possible embodiments of the modifications at the fibre core/fibre cladding boundary face are lines, curves and surfaces at a defined angle and lengths, as well as combinations of these embodiments.

According to a second aspect of the invention, the achievement of the above-mentioned object lies in an optical functional element having an optical waveguide, which has a first cross-sectional region with a first refractive index, a second cross-sectional region with a second refractive index, and a boundary region in the transition from the first to the second cross-sectional region, wherein at least a defined portion of the boundary region is provided with a modification at least of one optical property of the optical waveguide.

The optical functional element according to the invention is distinguished by the fact that the modification is provided in a boundary region in the transition from the first to the second cross-sectional region. In this manner, the coupling of laser radiation into the optical waveguide or the coupling of laser radiation out of the optical waveguide or both are locally influenced with microscopic precision. The directional dependency of the inward or outward coupling of laser radiation can be influenced in a purposeful manner by an appropriate choice of the modification of the optical properties in the boundary region. In another exemplified embodiment of the optical functional element according to the invention, a modification on a plurality of defined portions of the boundary region is provided in such a manner that of the modified boundary region portions a radial irradiation of defined, uniform light intensity takes place if light is coupled into the optical waveguide at one longitudinal end.

In another exemplified embodiment of the optical functional element of the invention, the modification is disposed at a plurality of defined portions of the boundary region in the longitudinal direction of the waveguide or in a direction perpendicular thereto or in both mentioned directions of the optical waveguide in such a manner that an optical grating, a spiral, a cross, a photonic bandgap structure, a combination of lines and dots, or a combination of the above-mentioned structures is provided.

The optical waveguide can contain, for example, materials such as quartz, glass, glass ceramics, one or more plastics, fluorides, or similar transparent materials, or combinations of materials.

In accordance with a third aspect of the invention, the object is achieved by a device for microstructuring an optical waveguide with laser radiation, wherein a laser constructed to emit at least one light pulse and a focussing device are provided in such a manner that laser radiation having a power density of roughly $10^{10}$ W/cm2 or of more than $10^{10}$ W/cm 2 can enter a presettable depth portion of an optical waveguide.

In a preferred embodiment of the device, in accordance with the third aspect of the invention the laser is constructed to emit light pulses with a duration of max. $10^{-10}$ seconds, preferably 0.1 to 50 ps. In another embodiment of the invention, the laser is constructed to emit light pulses having an energy of roughly 10 nj or less than 10 nj. In another embodiment of the invention, the frequency of the laser radiation is chosen to correspond to the material of the optical waveguide on the light path penetrated by radiation in the optical waveguide so that laser radiation with a power density of roughly $10^{10}$ W/cm$^2$ or of more than $10^{10}$ W/cm$^2$ can only enter the defined depth portion.

In another embodiment of the invention, a mounting for an optical waveguide is provided, which is constructed to hold the optical waveguide so that it is displaceable in its longitudinal direction or can rotate around its longitudinal axis, or both. In another embodiment of the invention, the focussing device is mounted for the performance of one or more of the following movements: a displacement in the direction of the spacing of the optical waveguide or in the longitudinal direction of the optical waveguide, or a rotation around its longitudinal axis.

BRIEF DESCRIPTION OF THE DRAWINGS

The invention is described in further detail below with reference to the drawings by means of exemplified embodiments. Therein.

DETAILED DESCRIPTION OF A PREFERRED EMBODIMENT

Figure 1:
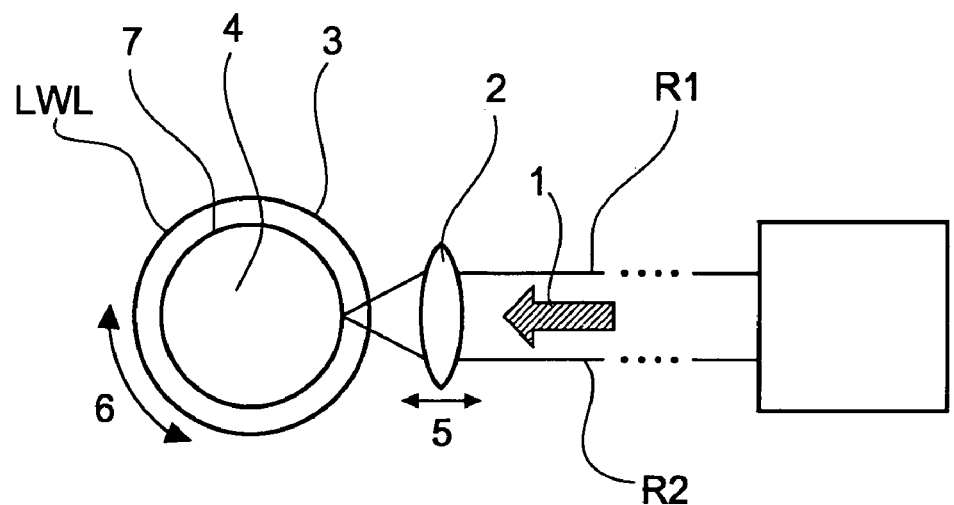
FIG. 1 shows a schematic representation of a device for microstructuring an optical waveguide.

FIG. 1 shows an exemplified embodiment of a device for the microstructuring of an optical waveguide. FIG. 1 is a schematic diagram. A laser L emits a laser beam. The laser beam is represented by marginal beams R1 and R2 and also by an arrow 1, which shows the beam direction. The laser beam is directed to an optical waveguide LWL by means of a microscope lens 2. In the present exemplified embodiment the optical waveguide comprises an optical waveguide cladding 3 and an optical waveguide core 4. The cladding 3 is constructed from a material having a lower refractive index than the core 4. In the transition from the cladding 3 to the core 4 there is a boundary region 7, which here is also called a boundary surface.

The distance between the microscope lens 2 and the optical waveguide LWL is adjustable, which is symbolised by the double arrow 5. The optical waveguide LWL is rotatably mounted around its longitudinal axis, which is symbolised by the double arrow 6. The microscope lens 2 is displaceable in the longitudinal direction of the optical waveguide.

By varying the distance of the microscope lens 2 from the boundary surface 7, the desired intensity and the most advantageous region in the transition between the optical waveguide core and the optical waveguide cladding can be set. Depending on the desired modification, apart from the focusing, the intensity of the laser beam can also be appropriately adjusted. For example, attenuation elements such as neutral grey filter can be used.

By a rotation 6 of the optical waveguide LWL, the modification can be produced with an extension in the circumferential direction of the optical waveguide LWL. Such a modification is also known as a radial modification. By displacing the microscope lens, a modification can be produced with an extension in the longitudinal direction of the optical waveguide LWL.

Figure 2:
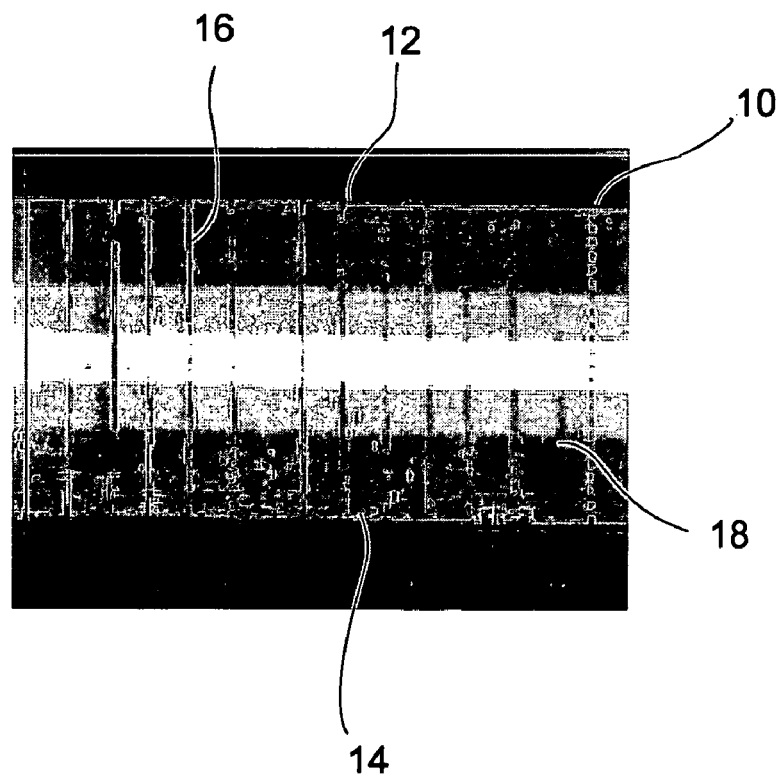
FIG. 2 shows a microscope photo of a quartz glass fibre modified by the method according to the invention.

FIG. 2 shows an exemplified embodiment of an optical waveguide 10 in a microscope photo. The optical waveguide 10 is a quartz glass fibre having a core with a diameter of 600 micrometers and a cladding with a diameter of 660 micrometers. The longitudinal direction of the optical waveguide 10 extends from the left-hand side to the right-hand side of the image in FIG. 2. For the represented photo the optical waveguide was penetrated by radiation transversely to the longitudinal direction. Transverse strips of different brightness in the picture that extend from the left-hand to the right-hand edge are primarily attributed to the radiation.

Vertical, dark stripes regularly spaced in the longitudinal direction of the fibre can be seen between an upper fibre edge 12 and a lower fibre edge 14. These stripes are modifications. In the transmitted light of the microscope they appear darker than the non-modified longitudinal portions of the fibre. Modifications 16 and 18 are marked as examples.

To produce the modifications, laser pulses of a wavelength of 800 nm, a pulse duration of 0.2 picoseconds, a single pulse energy of 2.3 µJ and a repetition rate of 1 kHz were used. The modifications were performed to different depths by the displacement of the microscope lens (40×, NA=0.63) in the direction of the fibre core. The greater depth of the modifications on the right-hand side of the picture can be seen, for example, at modification 18, which appears blurred in the photo in FIG. 3. However, modification 16, which was in the focus of the microscope during the photograph, appears sharp.

Figure 3:
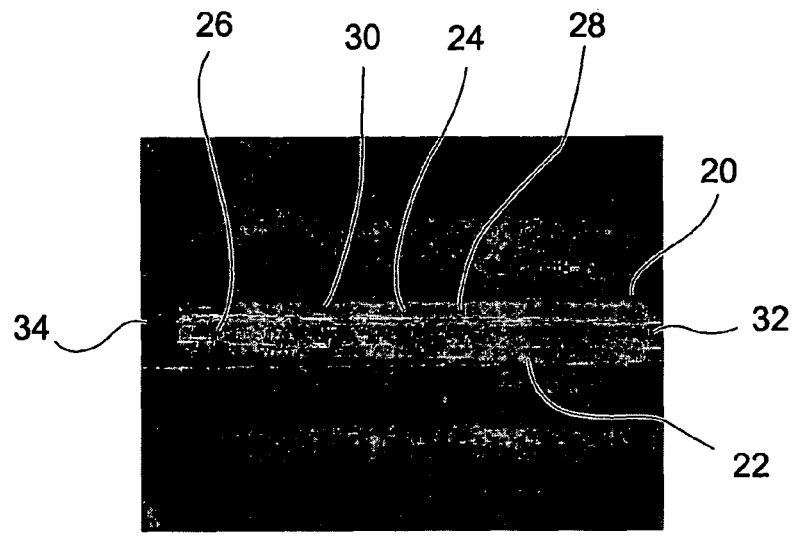
FIG. 3 shows a photo of modified regions of a quartz glass fibre, into the longitudinal side of which light is coupled.

FIG. 3 shows another exemplified embodiment of a quartz glass fibre 20 having laser-induced modifications. The quartz glass fibre 20 also has a core of 600 micrometers diameter and a cladding of 660 micrometers diameter. Here modifications were achieved with the aid of laser pulses having a basic wavelength of 800 nm, a pulse duration of 3 picoseconds and a single pulse energy of 3.8 µJ. The modifications took place with a spacing in the longitudinal direction of 10 micrometers over the entire circumference of the fibre 20.

The photo of FIG. 3 shows the radiation of light from the modified regions of the quartz glass fibres. For this a helium-neon laser is coupled in at the end of the fibre. Modified regions 22, 24 and 26, which are disposed one behind the other in the longitudinal direction of the fibre, can be clearly seen. A short portion 28 with a small number of modifications is disposed between the modified regions 22 and 24. Another short portion 30 with a smaller number of modifications is disposed between the portions 24 and 26. The regions 28 and 30 can be recognised from the fact that lesser radiation takes place from them and they therefore appear darker in FIG. 3. Dark portions 32 and 34, in which the fibre was not modified, can be seen at the left-hand and right-hand edge respectively in the extension of the modified regions.

Figure 4:
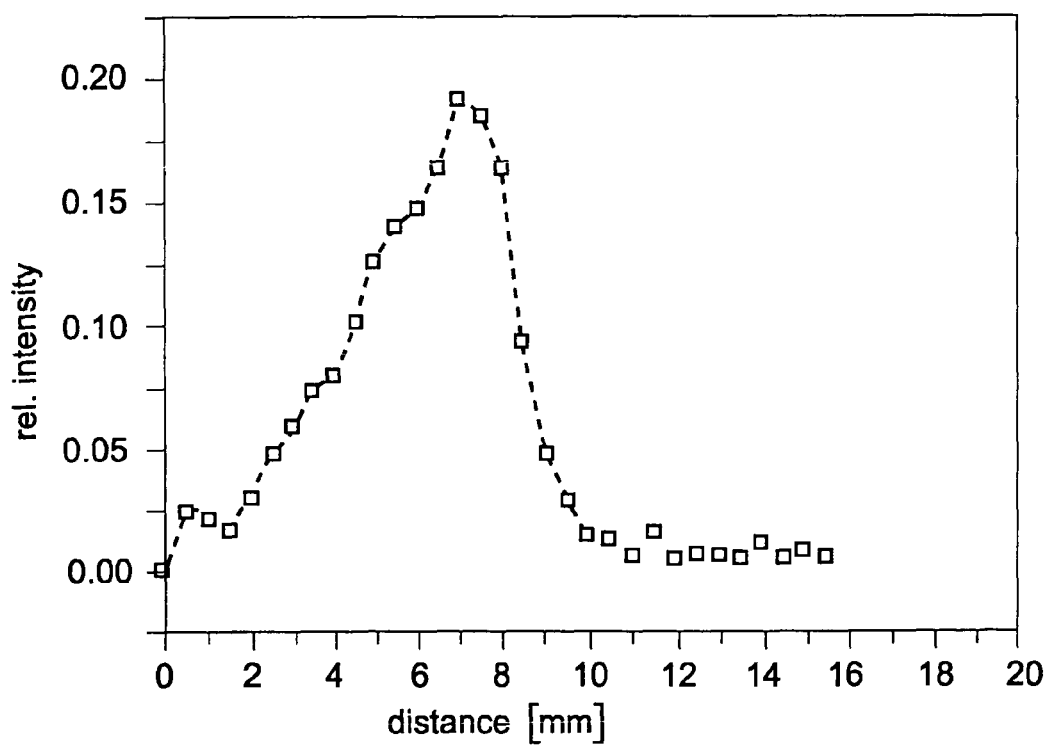
FIG. 4 shows a diagram of the radiated power of the fibres from FIG. 2 in relationship to the power coupled into the fibre as a function of the place of modification.

FIG. 4 shows a diagram in which the entire radiated power of the fibre 20 from FIG. 3 in relation to the power of the laser beam of the helium-neon laser which is coupled into the fibre is represented on the ordinate (Y axis). The distance in the longitudinal direction of the measurement point from one longitudinal end of the modified region of the fibre is entered on the abscissa (X axis). The radiation begins in the radial direction coming from great distances (corresponding to the direction of propagation of the laser beam in the fibre) at a distance of 10 mm and reaches a maximum with a distance of roughly 7 mm. Towards low spacing values, the radially radiated intensity decreases and has reached a relative intensity of only 10% at the end of the modification region. This is attributed to the fact that the radiation in the modified regions, which lie closer to the helium-neon laser, is so high that a considerable part of the radiated power is coupled out of the fibre by virtue of the radial radiation in these regions. With a greater distance of the helium-neon laser, the relative intensity of the outwardly coupled laser light therefore also necessarily drops.

The invention claimed is:

1. A method for the micro structuring of an optical waveguide to produce an optical waveguide having a first cross-sectional region with a first refractive index, a second cross-sectional region with a second refractive index, a protective buffer, and a boundary region in the transition from the first to the second cross-sectional region, wherein said first cross-sectional region is composed of undoped silica, wherein at least one defined portion of the boundary region is provided with a modification of at least one optical property of the optical waveguide, said modification being a non-periodic distribution, formed by a defined portion of the boundary region defining at least one of (i) microdamage, and (ii) a surface defined by the removal of material from the defined portion, comprising the steps of:

providing an optical waveguide comprising a first cross-sectional region having a first refractive index, a second cross-sectional area having a second refractive index, a protective buffer, and a boundary region in the transition from the first to the second cross-sectional area, exposing the optical waveguide through its protective buffer to laser radiation in the form of at least an ultra-short single pulse or a sequence of ultra-short pulses with a defined energy input;

at least one of microdamaging and removing the material from the defined portion of the boundary region with said laser radiation: and modifying at least one optical property of the optical waveguide at one said defined portion at least of the boundary region as a result of the step of exposing the optical waveguide to laser radiation, without removing said waveguide's protective buffer.

2. The method according to claim 1, wherein the modifying step includes changing the refractive index of the material of the first or of the second cross-sectional region or both.

3. The method according to claim 1, wherein the modifying step includes creating a scattering center by said microdamage or by said removal of material.

4. The method according to claim 1, wherein the modification step includes transforming the phase of the material of the first or of the second cross-sectional region.

5. The method according to claim 1, further comprising the step of selecting the laser radiation in such a manner that at the defined portion of the boundary region a charge carrier plasma with a charge carrier density dependent on the desired modification is produced.

6. The method according to claim 5, in which the laser radiation comprises a power density of roughly $10^{10}$ W/cm$^2$ or of more than $10^{10}$ W/cm$^2$.

7. The method according to claim 6, in which the laser radiation comprises single pulses having a duration of roughly $10^{70}$ seconds or of between 0.1 ps and 50 ps and an energy of roughly 10 nanojoules (nj) or less than 10 nanojoules (nj).

8. The method according to claim 6, further comprising the step of selecting the wavelength of the laser radiation is chosen so that the optical waveguide is transparent in the light path up to the defined portion of the boundary region for light of the chosen selected wavelength up to a power density of roughly $10^{16}$ W/cm$^2$.

9. The method according to claim 1, further comprising the step of focusing a laser beam is focused onto the defined portion of the boundary region by means of a microscope lens.

10. The method according to claim 1, further comprising the step of irradiating a laser beam is irradiated so that it enters the optical waveguide at an angle of 90° to an outer face of said optical waveguide at the point of impact.

11. The method according to claim 1, further comprising the step of guiding a laser beam through an immersion fluid before entering into the optical waveguide.

12. The method according to claim 1, further comprising the step of producing the modification in such a manner that at the respective portion of the boundary region light can be coupled out of the waveguide or that light can be coupled into the waveguide at the respective portion of the boundary region, or that light can be coupled in and also coupled out at the respective portion of the boundary region.

13. The method according to claim 1, further comprising the step of producing the modification on a plurality of defined portions of the boundary region in such a manner that from the modified boundary region portions a radial radiation of defined, uniform light intensity takes place when light is coupled into the optical waveguide at one longitudinal end.

14. The method according to claim 1, further comprising the step of producing the modification is produced at a plurality of defined portions of the boundary region in a longitudinal direction of the optical waveguide, or in a direction perpendicular thereto, or in both mentioned directions of the optical waveguide, in such a mariner that an optical grating, a spiral, a cross, a photonic bandgap structure, a combination of lines and dots, or a combination of any of the above-mentioned structures, is produced.

15. The method according to claim 1, further comprising the step of moving the optical waveguide relative to the laser beam or moving the laser beam relative to the optical waveguide.

16. The method according to claim 1, in which the first cross-sectional portion is an optical waveguide core and the second cross-sectional portion is an optical waveguide cladding.

17. The method according to claim 1, in which the optical waveguide comprises from the inside to the outside more than two cross-sectional portions having different refractive indices and a corresponding number of boundary regions of adjacent cross-sectional portions, and wherein the method further comprises forming said modifications at more than one boundary region.

18. The method according to claim 1, in which the optical waveguide comprises a continuous cross-sectional profile of the refractive index, and in which the modification takes place in at least one pre-selected cross-sectional portion.

19. A micro-structured optical waveguide product manufactured according to the method of claim 1.

* * * * *